(12) United States Patent
Yeoman et al.

(10) Patent No.: US 9,694,085 B2
(45) Date of Patent: Jul. 4, 2017

(54) TARGETED THERAPEUTIC NANOPARTICLES

(71) Applicant: nanoDERM Sciences, Inc., Derwood, MD (US)

(72) Inventors: Roy R. Yeoman, Burke, VA (US); Richard A. Winchurch, Lutherville, MD (US)

(73) Assignee: nanoDERM Sciences, Inc., Derwood, MD (US)

( * ) Notice: Subject to any disclaimer, the term of this patent is extended or adjusted under 35 U.S.C. 154(b) by 0 days.

(21) Appl. No.: 14/847,213

(22) Filed: Sep. 8, 2015

(65) Prior Publication Data

US 2016/0106852 A1  Apr. 21, 2016

Related U.S. Application Data

(63) Continuation of application No. 13/943,074, filed on Jul. 16, 2013, now Pat. No. 9,161,962, and a continuation-in-part of application No. 13/286,320, filed on Nov. 1, 2011, now Pat. No. 8,821,933.

(60) Provisional application No. 61/672,177, filed on Jul. 16, 2012, provisional application No. 61/344,872, filed on Nov. 1, 2010.

(51) Int. Cl.

| | |
|---|---|
| *A61K 47/48* | (2006.01) |
| *A61K 31/713* | (2006.01) |
| *A61K 39/44* | (2006.01) |
| *A61K 49/00* | (2006.01) |
| *A61K 38/12* | (2006.01) |
| *A61K 45/06* | (2006.01) |
| *A61K 9/06* | (2006.01) |
| *A61K 47/36* | (2006.01) |
| *B82Y 5/00* | (2011.01) |
| *C08B 37/02* | (2006.01) |
| *C08J 3/075* | (2006.01) |
| *C08L 5/02* | (2006.01) |
| *C08L 63/00* | (2006.01) |
| *C08G 65/332* | (2006.01) |

(52) U.S. Cl.
CPC ............ *A61K 47/4823* (2013.01); *A61K 9/06* (2013.01); *A61K 31/713* (2013.01); *A61K 38/12* (2013.01); *A61K 39/44* (2013.01); *A61K 45/06* (2013.01); *A61K 47/36* (2013.01); *A61K 47/48176* (2013.01); *A61K 47/48569* (2013.01); *A61K 47/48784* (2013.01); *A61K 47/48853* (2013.01); *A61K 47/48907* (2013.01); *A61K 47/48923* (2013.01); *A61K 49/0017* (2013.01); *B82Y 5/00* (2013.01); *C08B 37/0021* (2013.01); *C08G 65/3322* (2013.01); *C08J 3/075* (2013.01); *C08L 5/02* (2013.01); *C08L 63/00* (2013.01); *C08J 2305/02* (2013.01); *Y10T 428/2982* (2015.01)

(58) Field of Classification Search
USPC .............................................. 424/130.1, 487
See application file for complete search history.

(56) References Cited

U.S. PATENT DOCUMENTS

| | | | |
|---|---|---|---|
| 6,696,089 B2 | 2/2004 | Kabanov et al. | |
| 2004/0247683 A1 | 12/2004 | Popescu et al. | |
| 2005/0053590 A1 | 3/2005 | Meininger | |
| 2005/0249721 A1* | 11/2005 | Houston ................. | A61K 9/127 424/130.1 |
| 2009/0169635 A1 | 7/2009 | Schwarz et al. | |
| 2010/0009007 A1 | 1/2010 | Darvari et al. | |
| 2012/0107369 A1 | 5/2012 | Yeoman, III et al. | |

FOREIGN PATENT DOCUMENTS

WO          9637233 A1      11/1996

OTHER PUBLICATIONS

Kim et al., "Temperature-responsive and degradable hyaluronic acid/Pluronic composite hydrogels for controlled release of human growth hormone." Journal of Controlled Release 80 (2002); 69-77.
Raemdonck et al., "Advanced nanogel engineering for drug delivery." Soft Matter 2009:5; 707-715.
Sharma, A. et al., "Toxicological considerations when creating nanoparticle based drugs and drug delivery systems." Jan. 2012, vol. 8, No. 1, pp. 47-69.
Jain, A. et al., "Design and development of ligand-appended polysaccaridic nanoparticles for the delivery of oxaliplatin in colorectal cancer." Nanomedicine: Nanotechnology, Nanotechnology, Biology and Medicine, 2010, vol. 6, pp. 179-190.
Davis, S. S. et al., "Polymers in drug delivery." Current Opinion in Colloid & Interface Science, 1996, vol. 1, pp. 660-666.
Mudshinge, S. R. et al., "Nanoparticles: emerging carriers for drug delivery." Saudi Pharmaceutical Journal, 2011, vol. 19, pp. 129-141.
D1: Lin, C. et al., "Thermosensitive in situ-forming dextran-pluronic hydrogels through Michael addition." Mat. Sci. Eng. C, 2010, vol. 30, pp. 1236-1244.
AE Jung Huh et al., "Nanoantibiotics": A new paradigm for treating infectious diseases using nanomaterials in the antibiotics resistant era, Journal of Controlled Release, vol. 156, No. 2, Jun. 29, 2011, pp. 128-145, XP028112005, ISSN: 0168-3659, DOI: 10.1016/J.JCONREL.2011.07.002.

(Continued)

*Primary Examiner* — Walter Webb
(74) *Attorney, Agent, or Firm* — Bernard G. Pike; Pike IP Law, PLLC

(57) ABSTRACT

Disclosure of methods and compositions related to chemical conjugations to nanoparticles of polysaccharides cross-linked to poloxamers as well as nano-sized colloids comprised of polysaccharides and poloxamers. The nanoparticles may be produced by various methods including inverse miniemulsion polymerization processes which create nanogels of desired size, shape, and stability for controlled therapeutic drug delivery, imaging, and theragnostic applications.

9 Claims, No Drawings

(56) References Cited

OTHER PUBLICATIONS

Extended European Search Report dated Feb. 26, 2016 for corresponding European application No. 13820121.5-1453/2872120; PCT/US2013050647.

* cited by examiner

US 9,694,085 B2

SEQUENCE LISTING

```
<160> NUMBER OF SEQ ID NOS: 9

<210> SEQ ID NO 1
<211> LENGTH: 23
<212> TYPE: DNA
<213> ORGANISM: Escherichia coli

<400> SEQUENCE: 1
agggtgacgt caaagtggat acg                                              23

<210> SEQ ID NO 2
<211> LENGTH: 19
<212> TYPE: RNA
<213> ORGANISM: Artificial Sequence
<220> FEATURE:
<223> OTHER INFORMATION: Escherichia coli, Pseudomonas aerug

<400> SEQUENCE: 2
```

```
ggugacguca aaguggaua                                              19

<210> SEQ ID NO 3
<211> LENGTH: 19
<212> TYPE: RNA
<213> ORGANISM: Artificial Sequence
<220> FEATURE:
<223> OTHER INFORMATION: Escherichia coli, Pseudomonas aerug

<400> SEQUENCE: 3
ccacugcagu uucaccuau                                              19

<210> SEQ ID NO 4
<211> LENGTH: 23
<212> TYPE: DNA
<213> ORGANISM: Artificial Sequence
<220> FEATURE:
<223> OTHER INFORMATION: Escherichia coli, Pseudomonas aerug

<400> SEQUENCE: 4
gacttgaatc caccggtaga ttt                                         23

<210> SEQ ID NO 5
<211> LENGTH: 20
<212> TYPE: RNA
<213> ORGANISM: Artificial Sequence
<220> FEATURE:
<223> OTHER INFORMATION: Escherichia coli, Pseudomonas aerug

<400> SEQUENCE: 5
cuugaaucca ccgguagaud                                             20

<210> SEQ ID NO 6
<211> LENGTH: 19
<212> TYPE: RNA
<213> ORGANISM: Artificial Sequence
<220> FEATURE:
<223> OTHER INFORMATION: Escherichia coli, Pseudomonas aerug

<400> SEQUENCE: 6
ccacugcagu uucaccuau                                              19

<210> SEQ ID NO 7
<211> LENGTH: 23
<212> TYPE: DNA
<213> ORGANISM: Artificial Sequence
<220> FEATURE:
<223> OTHER INFORMATION: Escherichia coli, Pseudomonas aerug

<400> SEQUENCE: 7
gagcatgatg tacggatttc aac                                         23

<210> SEQ ID NO 8
<211> LENGTH: 19
<212> TYPE: RNA
<213> ORGANISM: Artificial Sequence
<220> FEATURE:
<223> OTHER INFORMATION: Escherichia coli, Pseudomonas aerug

<400> SEQUENCE: 8
gcaugaugua cggauuuca                                              19

<210> SEQ ID NO 9
<211> LENGTH: 19
<212> TYPE: RNA
<213> ORGANISM: Artificial Sequence
```

```
<220> FEATURE:
<223> OTHER INFORMATION: Escherichia coli, Pseudomonas aerug

<400> SEQUENCE: 9
cguacuacau gccuaaagu                                              19
```

TARGETED THERAPEUTIC NANOPARTICLES

RELATED APPLICATIONS

This patent application is a continuation of pending U.S. patent application Ser. No. 13/943,074 filed on Jul. 16, 2013, which claims priority under 35 U.S.C. 119 to U.S. Provisional Patent Application No. 61/672,177 entitled "Conjugation of Polymers and Hydrogels" filed on Jul. 16, 2012, hereby incorporated by reference in its entirety, and under 35 U.S.C. 120 to U.S. patent Ser. No. 13/286,320 entitled "Polymers and Hydrogels" filed on Nov. 1, 2011, hereby incorporated by reference in its entirety, which claims priority under 35 U.S.C 119 to U.S. Provisional Patent Application No. 61/344,872 filed on Nov. 1, 2010, hereby incorporated by reference in its entirety.

TECHNICAL FIELD

The invention is related to therapeutic drug delivery technologies. Polysaccharide-poly(epoxide) or more specifically, polysaccharide-poloxamer, nanogels may be functionalized with ligands and/or targeting agents to provide a biodegradable, and thermally responsive drug delivery. The hydrogel nanoparticles can be "functionalized to target" specific desired body sites for the controlled release of encapsulated therapeutic cargo.

BACKGROUND

The use of antibiotics in the treatment of infectious disease has increased greatly over the past fifty years. Due to the ubiquitous use, bacteria have developed resistance to the antibiotics commonly administered to treat bacterial infections. Antimicrobial resistance has been reported for all known antibacterial drugs currently available.

The global infectious disease treatment market is now over $100 billion, and by 2014 is expected to be $138 billion. According to the Centers for Disease Control and Prevention (CDC), each year in the US alone more than 2 million people acquire hospital-acquired infections (HAI) of which almost 100,000 die. Estimated costs associated with HAI in the US are as high as $30 billion annually. HAI and other infections are most often caused by gram-negative bacteria, but can also occur from other bacteria, viruses, fungi and parasites.

The annual cost of antibiotic-resistant infections in the US healthcare system has recently been calculated to be in excess of $20 billion. The widespread use of antibiotics, especially broad-spectrum antibiotics, is believed to have played a significant role in the emergence of resistant bacteria.

An effective delivery system for antimicrobials would target susceptible microorganisms rather than a systemic delivery to the entire body. This delivery system will allow for lower levels of the agents, reduce the exposure to beneficial organisms and minimize the development of drug-resistant strains of pathogens. The concept of a "magic bullet" delivery system has been widely discussed in the literature but, unfortunately, few strategies have proven successful. Drug activity is a result of molecular interaction(s) in certain cells. The drug must reach the cellular site of action at sufficient concentrations following oral, intravenous, local, transdermal, or other means of administration. The aim of drug delivery is to deliver the drug at the specific site of action, at the right concentration, and for the effective period of time.

One method that has been employed is the use of monoclonal antibodies with specificities directed toward specific antigenic sites on the targets. This presumes that antigenic sites on the targets can be defined and that for each pathogen unique antibodies can be produced that are directed toward these sites with minimal cross-reactivity. These goals are not easily achieved. Nonetheless, a system that can optimize cellular targeting, maintain effective intracellular antimicrobial concentrations and provide resistance to inhibit multiple targets within multiple classes of pathogens is a goal widely sought.

Gram negative bacterial pathogens constitute the most ubiquitous and serious sources of infection in civilian and military populations. Gram-negative bacteria have an outer membrane that protects them from antibiotics and detergents. All gram negative bacteria exhibit endotoxin or lipopolysaccharide (LPS) in their outer membrane. Endotoxin is composed of complex carbohydrates and a lipid. The carbohydrates vary in structure and confer the antigenic properties which distinguish different bacterial strains. The lipid is highly conserved across strains and is responsible for many of the pathogenic effects of endotoxin. Lipid A is the most common lipid moiety in gram negative bacteria and is a potent pyrogen and a polyclonal B lymphocyte activator. The ubiquitous nature of endotoxin makes it an attractive target for treatment of nearly all gram negative bacterial strains.

There exists a need for a pharmaceutical drug delivery system that can target specific cells and deliver treatment to the targeted cells.

SUMMARY

In one aspect, the invention is directed to nanoparticle drug delivery systems. The drug delivery system may comprise a nanogel targeting molecule or nanoparticle. In one embodiment, the nanogel targeting molecule comprises a polymeric network. The polymeric network may comprise a plurality of first block copolymeric segments derived from epoxide monomers and a plurality of second polymeric segments derived from polysaccharides. Further the drug delivery nanoparticle may comprise targeting agents chemically attached to the polymeric network.

In certain embodiments of the polymeric network, the block copolymer of epoxides is a triblock copolymer. The block copolymer may comprise at least one block derived from propylene oxide monomers and at least one block derived from ethylene oxide monomers. In a further embodiment, the block copolymer of epoxides is an ABA triblock copolymer wherein the A block is derived from ethylene oxide monomers and the B block is derived from propylene oxide monomers, such as a poloxamer. Embodiments of the nanogels and nanoparticles may be thermally responsive or degradable at human body temperatures such as in a range of 96° F. to 100° F.

The hydrogel or hydroparticle may comprise polysaccharide monomers in addition to the poly(epoxide) monomers. Polysaccharides are long carbohydrate molecules of monosaccharide units joined together by glycosidic bonds that range in structure from linear to highly branched. Polysaccharides are often quite heterogeneous, containing slight modifications of the repeating unit. Dextran is a colloidal, hydrophilic, and nontoxic polysaccharide that may be enzymatically degraded in the human body dextranase. Dextran is composed of linear α-1, 6-linked D-glucopyranose residues with a low fraction of −1,2, −1,3 and −1,4 linked side chains. Dextrans, as well as other polysaccharides, have a plurality of hydroxyl groups that can be directly reacted to add functional groups to the dextran backbone or may be modified to form reactive end groups which may be used for cross-linking or otherwise functionalizing the hydrogel. For example, the saccharide may be functionalized allyl isocyanate (Al), ethylamine (AE), chloroacetic acid (AC) and/or maleic anhydride (AM). Dextran fulfills many of the ideal characteristic features of a good carrier candidate. It is nontoxic, nonimmunogenic and nonantigenic.

The nanoparticles may be functionalized with groups that are capable of binding with a receptor on a cell (hereinafter "targeting agents" or "ligand") chemically attached to the nanogel or nanoparticle. The nanogel or nanoparticle comprising chemically attached targeting agent may then be considered a targeting molecule. In a specific embodiment, the hydrogel targeting molecule comprises polymeric segments derived from dextran and polymeric segments derived poloxamers that are cross-linked and a targeting agent chemically attached to the polymeric network. The soft cell properties of dextran and the stabilizing, thermally responsive properties of poloxamers and poly(epoxides) offer a safe, non-toxic, and controlled drug delivery vehicle. Polysaccharide-poloxamer hydrogels, nanogels, and nanoparticles are biodegradable, bioabsorbable and will deteriorate to elements naturally excreted or absorbed by the body allowing release of medicaments at the targeted site.

Targeting agents of the nanogels or nanoparticles are capable of binding to a receptor in the body. As used herein, a receptor is a molecule or a portion of a molecule found on the surface of a cell that receives chemical signals from substances outside the cell. When targeting molecule binds to a receptor, they direct the cell to do something, such as divide, die, or allow specific substances to enter or exit the cell. Binding to the receptor may be through covalent bonding, ionic bonding, complexation, hydrogen bonding, dipole-dipole interaction, van der Waals forces or any combination of such associations between at least one site of the targeting agent and at least one site of the receptor, as long as the binding is sufficiently strong to essentially form a target-receptor associate and activate the receptor. The targeting agent may be polymyxin B or a monoclonal, for example.

In additional embodiments, the nanoparticle drug delivery system comprises medicaments. The medicaments may be chemically attached to or encapsulating within the nanogel. The targeting agent attaches the nanoparticle to the target receptor and the medicaments may be released from the nanogel or nanoparticle as the poloxamer based segment is thermally or otherwise degraded and the dextran based segment is enzymatically degraded. This provides a drug delivery system with targeted medicament delivery. The medicaments may be for therapeutic treatment of a wide variety of diseases and ailments that would benefit from such targeted delivery. For example, the medicament may be at least one of a pharmaceutical, nicotinic acid, glucocorticoids and other budesonides, mitomycin C, monoclonal antibodies, anti-inflammatory agents, naproxen, aspirin, ketoprofen, ibuprofen, diclofenac, indomethacin, a prodrug, a fluorescent labeling agent or radiotag biomarker. The nanoparticle targeting nanogel or nanoparticle may have an average diameter in the range of 1 nanometer to 1000 nanometers or the nanogel targeting molecule may have an average diameter in a range from 20 nanometers to 250 nanometers, for example. An optimal size of hydrogel nanoparticles for prolonged in vivo blood residence is in the 20-200 nm range.

In another embodiment, enzymes may be medicaments chemically attached or encapsulated into the polysaccharide-poly(epoxide), polysaccharide-poloxamer or dextran-pluronic F-127 hydrogel and/or nanoparticles. The enzymes may be conjugated to dextran or poloxamers monomers prior to polymerization or attached to the surface of the nanogel or nanoparticle. Enzymes that may be chemically attached to or encapsulated within the hydrogel include, but are not limited to, α-amylase, arginase, asparaginase, carboxypeptidase, catalase, β-galactosidase, hyaluronidase, NAD+, streptokinase, papain, α-chymotrypsin and trypsin. In other embodiments, dextran may be functionalized to attach prodrugs by preparing carboxymethyl dextran, dextran sulphate, or diethylaminoethyl dextran. Diethylaminoethyl dextran is an example of a charged dextran derivative that may form complexes with various chemical entities including, for example, bleomycin, isometamidium and gentamicin may form a dextran sulphate complexes and proteins and nucleic acids that may be chemically attached to the hydrogel or nanoparticle. Hormones that also may be linked to the hydrogel include, but are not limited to, oxytocin and vasopressin.

Polymyxins may be conjugated to the hydrogel. Polymyxins are antibiotics, with a general structure consisting of a cyclic peptide with a hydrophobic tail. They disrupt the structure of the bacterial cell membrane by targeting its phospholipid receptors. Polymyxins are produced by nonribosomal peptide synthetase systems in gram-positive bacteria such as *Paenibacillus polymyxa* and are selectively toxic for Gram-negative bacteria due to their specificity for the lipopolysaccharide molecule that exists within many gram-negative outer membranes.

Polymyxins B and E (also known as colistin) are used in the treatment of gram-negative bacterial infections. The global problem of advancing antimicrobial resistance has led to a renewed interest in their use recently.

The invention is also directed to a method of forming a nanoparticle drug delivery system. In one embodiment, the process is directed to a miniemulsion polymerization process, such as, but not limited to, a radical polymerization miniemulsion process or a controlled radical polymerization process such as atom transfer radical polymerization. In another embodiment, polysaccharides are copolymerized with poloxamers in an inverse miniemulsion process. The polysaccharide may be functionalized with polymerizable functional groups and/or other functional groups such as medicaments or targeting agents prior to, during, or after polymerization. Similarly, the poloxamer may be functionalized with polymerizable functional groups and/or other functional groups such as medicaments or targeting agents prior to, during, or after polymerization.

Miniemulsion polymerization processes are conducted in specially formulated heterophase systems consisting of stable nanodroplets suspended in a continuous phase. The narrowly size distributed nanodroplets of 50 to 500 nm may be prepared by a shearing system containing oil, water, a surfactant, and an osmotic pressure agent which is insoluble in the continuous phase.

Hydrogel nanoparticles are solid colloidal drug carriers, ideally in the range of 20 to 120 nm in average diameter, whereby a drug may be encapsulated within the core nanodomain and/or conjugated to the hydrogel network.

Nanoparticles comprising dextran (polysaccharides) and Pluronic® F127 (poloxamers) may be produced via emulsion (colloidal) process polymerization. For IV applications the poloxamer, Pluronic® F68, can be utilized for nanoparticle production by the same process. The small molecular weight poloxamer should produce nanoparticles suitable for IV administration.

DESCRIPTION

Versatile hydrogels and nanogels comprising cross-linked polysaccharides and epoxide polymers is described in U.S. patent application Ser. No. 13/286,320 entitled "Polymers and Hydrogels" and is hereby incorporated by reference in entirety. In one embodiment, modified dextran monomers and modified poloxamer, Pluronic® F-127, are cross-linked to form a hydrogel. This is an interesting hydrogel as both dextran and Pluronic® F-127 have been approved for use by the FDA and a hydrogel formed from these compounds offers a controlled drug delivery platform that is nontoxic, biodegradable, and thermally responsive at normal human body temperatures.

An embodiment of a polysaccharide-poloxamer hydrogel is shown in Chemical Structure 1. A natural polymer, dextran is a colloidal, hydrophilic, and nontoxic polysaccharide composed of linear α-1, 6-linked D-glucopyranose residues with a low fraction of −1, 2, −1, 3 and −1, 4 linked side chains. Also dextran is biodegraded in the human body by dextranase. Dextran comprises a plurality of reactive hydroxyl groups (i.e., —OH group) that can be reacted with additional compounds to attach functional groups to the polymer backbone. These functional groups may react with other monomers to form hydrogels by any polymerization process, for example, via photochemical cross-linking.

Additionally, the dextran hydroxyl groups provide a vehicle for producing "tunable" hydrogels. The properties of the nanogels may be varied by varying the degree of cross-linking, the molecular weight of the polysaccharide and the poloxamer, the block lengths of the poloxamer, and the addition of any other monomers, and/or chemical linking groups, for example. Nanogels may be produced with different mechanical properties including, but not limited to, mechanical solubility, electric charge, partition coefficient, strength, swelling capacity, diffusion, thermal and/or enzymatic degradation, etc. The physico-chemical properties of the dextran-poloxamer hydrogel conjugates may be modified in order to guide the conjugate selectively to the targeted site to increase the efficacy of the targeting agent. The dextran-poloxamer hydrogel synthesis can be optimized per the specific application for controlled drug delivery and duration of prescribed therapy, e.g., various dextran-poloxamer varying the ration of dextran-poloxamer composition.

In one embodiment, poloxamer diacrylate may be reacted with a dextran acrylate to form the hydrogel.

Example 1: Pluronic F-127 Diacrylate Synthesis

Pluronic F-127 (poloxamer) obtained from BASF may be dissolved into a 10% solution with dichloromethane (DCM) in a 2-neck flask with a stir bar. Triethylamine (TEA) and acryloyl chloride may be added to the flask in the molar proportion of 3× excess to the [—OH] end groups of the poloxamer and the flask stirred at 80° C. for 3 hours under reflux. After such acrylation, the solution may be filtered and precipitated in hexane to recover the poloxamer diacrylate and then dried to remove residual hexane. This reaction may also be performed with any soluble materials that possess alcohol groups, so other polymers may also be modified accordingly.

Example 2: Dextran Acrylate Synthesis

Commercially obtained dextran may be dissolved into a 10% solution with DMSO in a 2-neck flask with a stir bar. Triethylamine and acryloyl chloride were added to the flask in the molar proportion relevant to the number of [—OH] end groups which are desired to be acrylated (may be variable based upon the desired degree of cross-linking) and the flask may be stirred at 80° C. for 3 hours to allow sufficient conversion. After such acrylation, the dextran acrylate DMSO solution may be filtered and precipitated in isopropanol to purify the dextran-acrylate and subsequently dried. The grade and type of dextran may be chosen in order to control the properties as well as the degree of modification.

Other methods of hydrogel formation may also be used without monomer modification steps such as a radical polymerization process. Stable nanogels of desired size and shape maybe produced with an inverse mini-emulsion polymerization process such as a controlled radical polymerization inverse mini-emulsion process.

The polysaccharide-poloxamer hydrogel may further be conjugated with functional group targeting systems for site specific therapeutic drug delivery. More specifically, polysaccharide-poloxamer nanogels (nanogels are hydrogels which have an average diameter between 1 and 1000 nanometers) may be functionalized to be biocompatible, biodegradable, bioabsorbable and thermally responsive to body temperatures that will trigger a controlled release of medicaments.

Inverse emulsion polymerization may be used for fabrication via cross-linking of acrylate derivatives of dextran and diacrylate derivatives of poloxamers. This polymerization technique allows for control over size, is versatile in respect to initiation and composition, and may proceed to full double-bond conversion in a relatively short time. Incorporation of functional polysaccharide comonomers, like dextran, in the polymeric network affords the possibility of further conjugation, such as the addition of biomarkers, fluorescent labeling, and macromolecular prodrugs, for example. Moreover, hydrogel nanoparticles in the range of 50-250 nm may be designed to maintain a state of stability as aqueous dispersions, resist aggregation, and can be freeze-dried as solid powders for long-term storage without degradation.

Example 3: Dextran Modification for Further Reaction

Dextran may be functionalized directly through reaction with the hydroxyl groups or indirectly by reaction with a linking functional group and subsequent further functionalization. The hydroxyl groups may easily react with a variety of linking functional groups including, but not limited to, isocyanates and acyl chlorides. The dextran may be utilized with these groups or further functionalized on these linking functional groups. A generalized reaction for functionalizing dextran is shown below in Reaction 1. In this case "R" and "R1" are generally any group that has some desirable property to be applied for this process. These modifications are as follows:

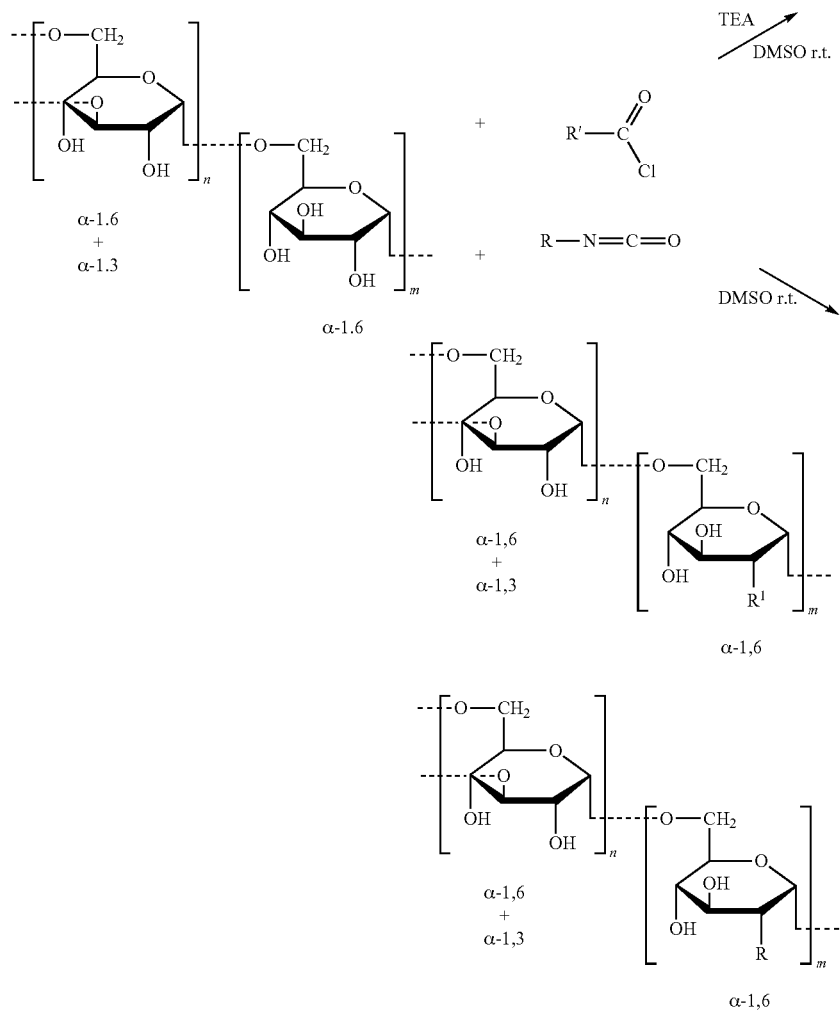

Reaction 1. Generic modification reactions of dextran.

Example 4: Copolymerization with Dimethylaminoethyl Methacrylate (DMEAMA) and SiRNA The poloxamer diacrylate (Example 1) and dextran acrylate (Example 2) monomers may be co-dissolved with DMEAMA and/or siRNA in an aqueous solution at various concentrations prior to polymerization. Additionally irgacure 2959 may be dissolved into this formulation at ~1-5% w/w monomers to make the resultant hydrogel photoactive.

Additional monomers may be substituted for or added in addition to the DMEAMA to provide additional properties to the resultant hydrogel, including, but not limited to, hydrogen bonding monomers (n-vinyl pyrrolidinone, acrylic acid), thermally sensitive monomers (N-isopropyl acrylamide), or additional cross-linking agents (polyethylene glycol diacrylate) so as to add or modify properties of the resultant particles. Examples of potential monomers are shown in Table 1.

TABLE 1

| Example monomer additives | | |
|---|---|---|
| Property | Monomer | Structure |
| Hydrophobic Solubilization/ plasticization modifiers | 4-aminosalicylic acid methylacrylate | ![structure] |
| | Styrene | ![structure] |

TABLE 1-continued

Example monomer additives

| Property | Monomer | Structure |
|---|---|---|
| | Stearyl methacrylate | $H_2C=C(CH_3)C(O)OCH_2(CH_2)_{16}CH_3$ |
| | Methyl methacrylate | $H_2C=C(CH_3)C(O)OCH_3$ |
| | Cyclohexyl methacrylate | cyclohexyl methacrylate structure |
| | Ethylene glycol phenyl ether methacrylate | $H_2C=C(CH_3)C(O)OCH_2CH_2OC_6H_5$ |
| | Poly(propylene glycol) methacrylate | $H_2C=C(CH_3)C(O)O[CH(CH_3)CH_2O]_nH$ |
| | Poly(propylene glycol) 4-nonylphenyl ethyl acrylate | |
| Hydrophilic components | Poly(ethylene glycol) methacrylate | $H_2C=C(CH_3)C(O)[OCH_2CH_2]_nOH$ |
| | Acrylamide | $H_2N-C(O)-CH=CH_2$ |
| Hydrophilic Muco-adhesive components | Acrylic acid | $H_2C=CH-C(O)OH$ |
| | N-vinyl-pyrrolidinone | N-vinyl-pyrrolidinone structure |
| Thermogelling components | N-isopropyl-acrylamide (NIPAM) | $H_2C=CH-C(O)NH-CH(CH_3)_2$ |

TABLE 1-continued

Example monomer additives

| Property | Monomer | Structure |
|---|---|---|
| | Vinyl-caprolactam (VCM) | vinyl-caprolactam structure |
| | 2-(Diethylamino) ethyl methacrylate | $H_2C=C(CH_3)C(O)OCH_2CH_2N(CH_2CH_3)_2$ |

Example 6: Exemplary Dextran Conjugation Chemical Processes

Direct Esterification

The dextran ester prodrugs of several drugs like nicotinic acid, naproxen, aspirin, ketoprofen, ibuprofen, diclofenac and indomethacin have been synthesized with the aim of achieving prolonged release properties. Dextran can be attached to the drug to form a prodrug by a direct linkage, attachment through linker group. In direct linkage model, drug is directly linked to the hydrogel, which would release the active agent in a predictable manner by thermal degradation, pH dependent hydrolysis, or other degradation of portions of the hydrogel.

Dextran can be attached to the drug to form a prodrug by a direct linkage, attachment through linker group or through covalent bonding, ionic bonding, complexation, hydrogen bonding, dipole-dipole interaction, van der Waals forces or any combination of such associations. In direct linkage model, drug is directly linked to the hydrogel, which would release the active agent in a predictable manner by thermal degradation, pH dependent hydrolysis, or other degradation of portions of the hydrogel.

Scheme 1: Synthesis of polysaccharide conjugates: Direct esterification

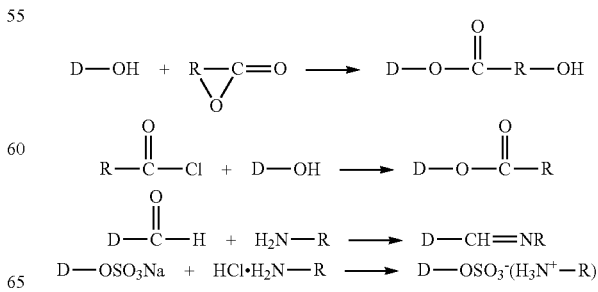

Carbonate Ester Method

Drugs containing a hydroxyl group can be coupled to dextran in the form of carbonate ester linkages either by activating the carrier hydroxyl group by phosgene followed by addition of alcoholic drug (Scheme 2) or by preparing chlorocarbonate dextran esters of the drug which are further used as intermediates in the construction of enzyme conjugates.

Periodate Oxidation Method

Dialdehyde dextran is obtained by periodate oxidation of dextran, which is condensed with amino compounds yielding schiff bases. The subsequent reduction with sodium borohydride is performed in order to stabilize the conjugate.

Scheme 2: Synthesis of polysaccharide conjugates: Carbonate ester method

Scheme I

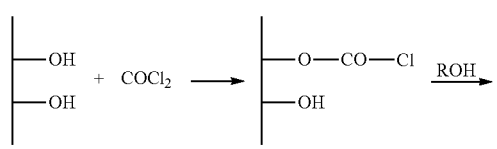

Scheme 3: Synthesis of polysaccharide conjugates: Periodate oxidation method

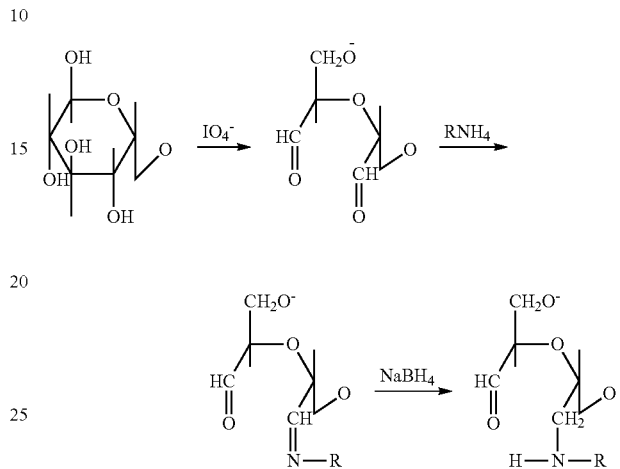

Scheme II

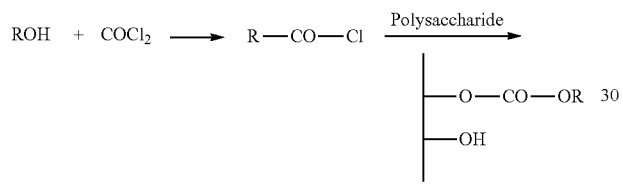

Carbamate Ester Method

The carbamate ester liganded conjugates exhibit prolonged duration of activity and reduced toxicity in proportion to the free drug. The principal routes to obtain dextran carbamate ester linkages are shown in Scheme 4.

Scheme 4: Synthesis of polysaccharide conjugates: Carbamate ester method

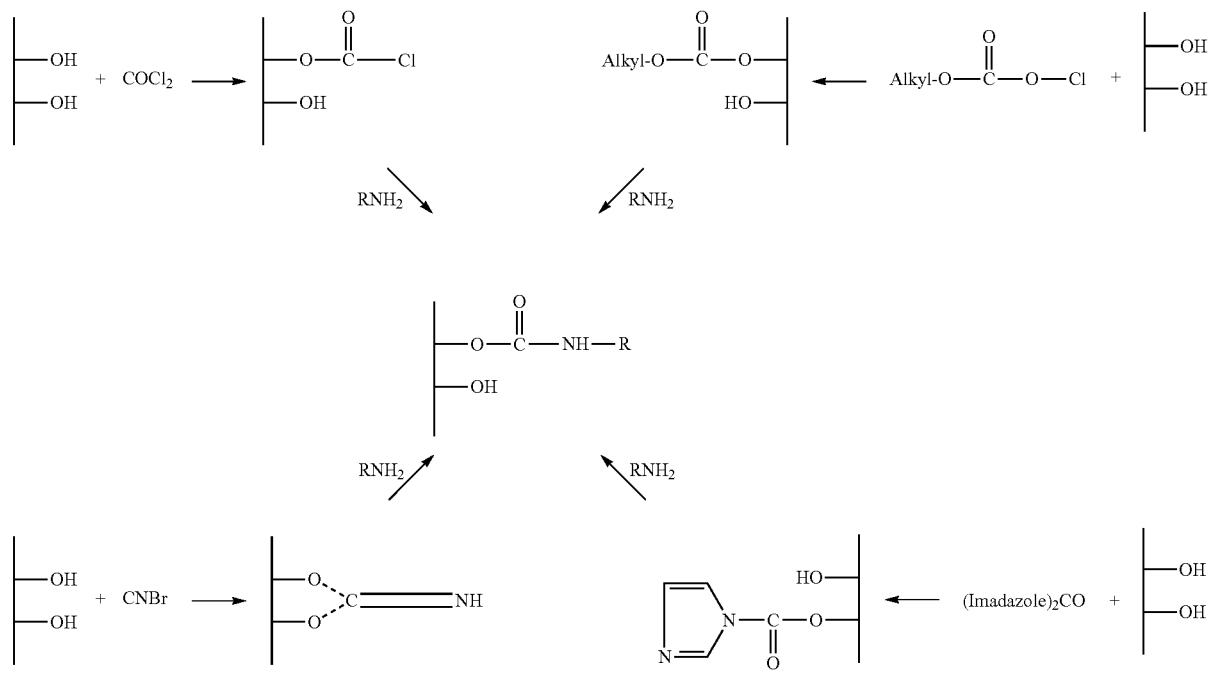

Bromide Activation Method:

The cyanogen bromide activation of dextran is probably the most widely used reaction to achieve covalent attachment of compounds possessing an amino function to dextran as shown in Scheme 5.

Scheme 5: Bromide activation method

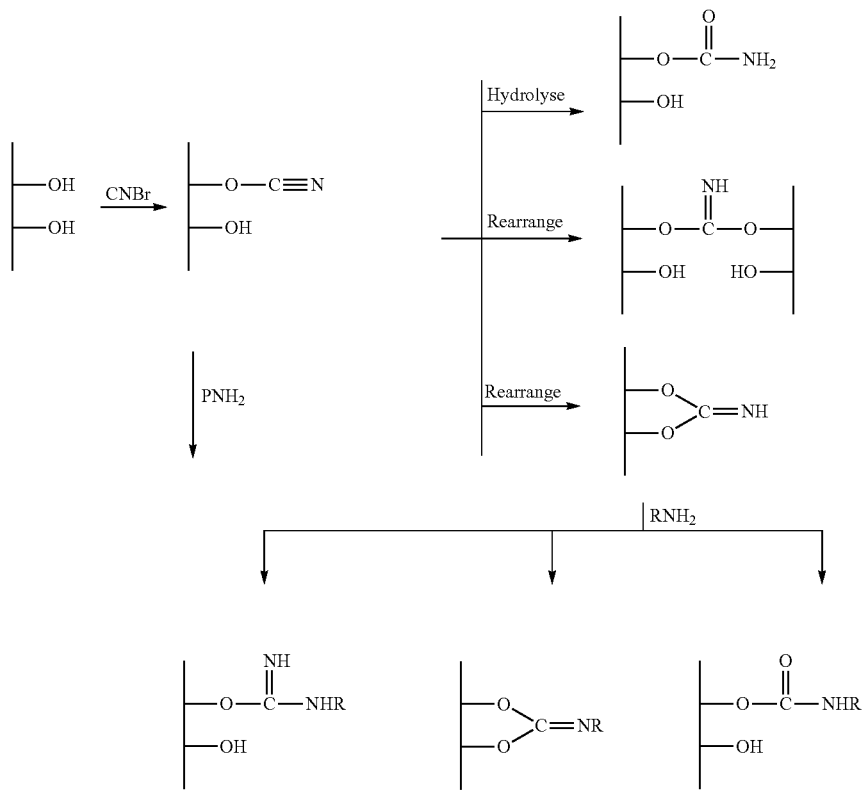

Acid Cleavable Linking Groups

Conjugates may be added to polysaccharides by acid cleavable functional groups such as shown in Scheme 6 to add prodrugs to the nanogel or nanoparticles.

Scheme 6: Acid cleavable acid group linking groups

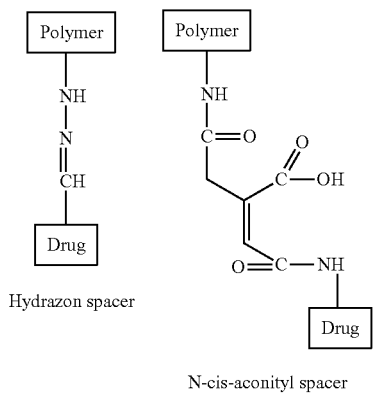

Targeted Conjugations of Dextran

As stated above, the chemical composition of polysaccharide-poloxamer hydrogels provides for chemical modifications for attaching targeting agents for receptors and attaching or encapsulating medicaments for therapeutic treatment of a wide variety of diseases and ailments. Dual conjugations may also be prepared, for example, a polysaccharide-poloxamer nanoparticle may comprise both a cancer cell luminescent biomarker conjugate and a cancer cell targeting prodrug conjugate for real time theranostics.

Additionally, Polymyxin B (PMB), shown in Formula 1, may be conjugated to a polysaccharide-poloxamer nanoparticle as shown in Formula 2. Polymyxin B is an antibiotic used against gram-negative bacterial infections. Polymyxin B is a targeting agent that binds to receptors on cell membranes of Gram Negative bacteria resulting in a change in its structure, making the cell wall more permeable.

Formula 1: Polymyxin B

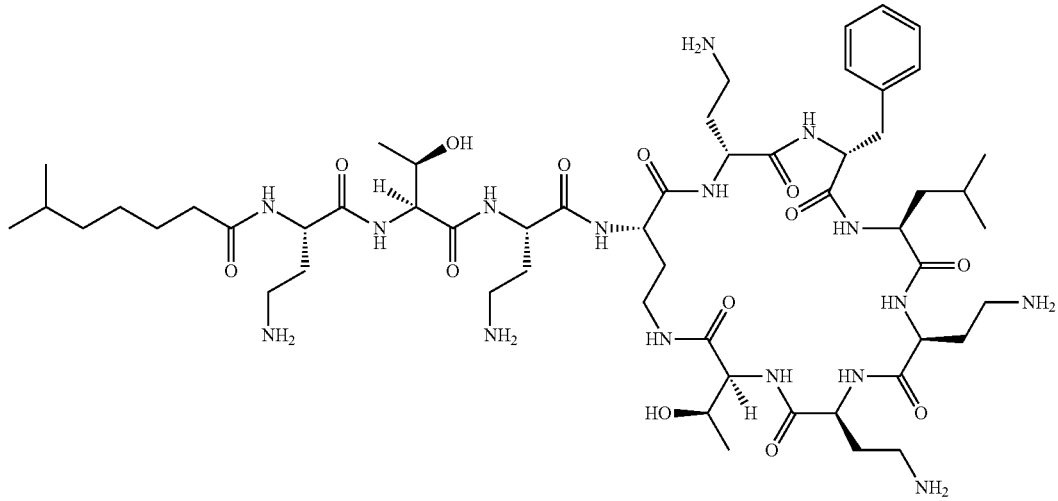

Formula 2: Polymyxin B (PMB) conjugated to polysarcharide-poloxamer hydrogel

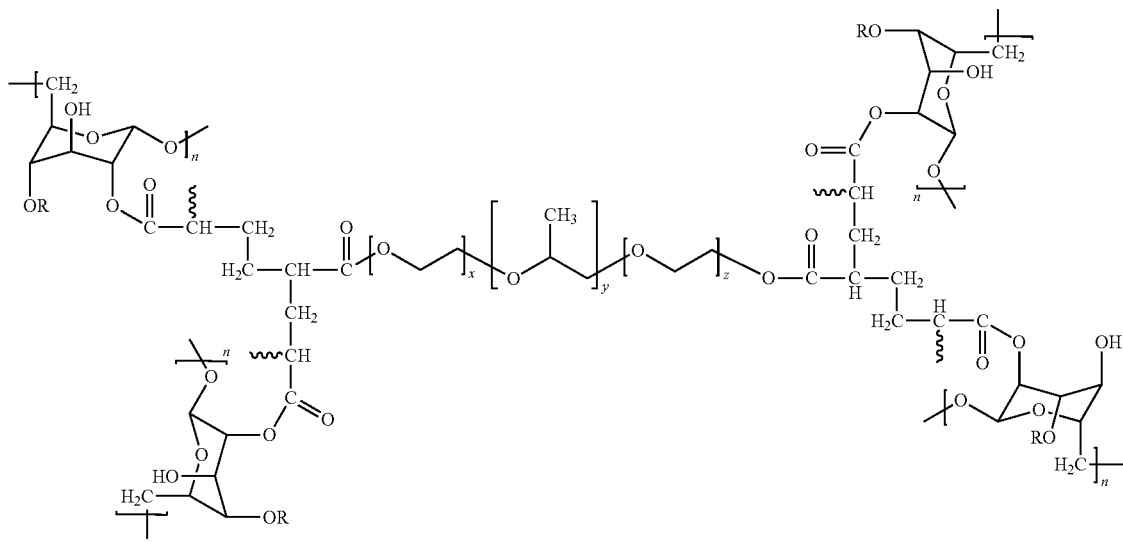

R = PMB

Example 6: Dextran-Polymyxin Conjugate Synthesis

The polysaccharide-poloxamer nanoparticle as shown in Formula 3 may be formed by conjugating the PMB to the monomers prior to the polymerization (as discussed in Examples 6 and 7) or by conjugating the PMB to the surface of the polysaccharide-poloxamer nanoparticle. For example, dextran acrylate (Example 2) may be dissolved in 20 ml water, cooled to 0° C., and 5-300 mg of 1-cyano-4-dimethylamino pyridinium tetrafluoroborate (CDAP) will be added and mixed for 30 seconds. TEA (0.2M, 0.04 ml per 5 mg CDAP) will be added dropwise with vigorous stirring, and the entire reaction mixture is transferred to 80 ml of ice cold ethanol containing 1 ml of 10N HCl. The dextran precipitates, and the precipitate is removed by cold centrifugation at 1000 g, for 5 min, and solubilized in 20-50 ml of 0.25M Na-bicarbonate buffer at pH 9.0. To this mixture 600-1000 mg of PMB (either powdered or solubilized in water) will be added and stirred for 24 hours at 8° C. The entire reaction mixture is then transferred to 50,000 molecular weight cut-off dialysis tubing and dialyzed against 0.05M pyrogen-free phosphate buffer for 6-10 days.

Example 7: Alternate Dextran-Polymyxin Conjugate Synthesis

Dextran acrylate (Example 2) may be dissolved in water and reacted with sodium periodate in order to generate functional aldehyde groups available for subsequent reaction. The thus activated dextran will then be dissolved in DMSO along with polymyxin-B and reacted to conjugate using a commercially available hetero-bifunctional photoaffinity cross-linker such as p-azidobenzoyl-hydrazide (ABH, Pierce). This solution will be handled in the dark and allowed controlled periods of exposure to UV light via Blak-Ray B100A. Polymyxin-B in double-distilled water (0.5) is combined with the heterobifunctional covalent ion crosslinking reagent azidohenzoyl hydrazide, 50 μL of 50 mM in DSMO. Following constant stirring in a 37° C. water bath for 60 min, the preparation is exposed to light-flashes (5×3 sec) from a halogen lamp source. Preparation of Hydrogel involved limited oxidation under dark conditions with sodium periodate (NaIO4 30 mM, pH 7.0, 1.0 mL). During the final phase (II) of the semisynthesis procedure, the polymyxin-azidohenzoyl hydrazide reactive intermediate complex was combined with partially oxidized Hydrogel fractions and the resulting reaction mixture was stirred continuously at 24° C. for 30 minutes.

Example 8: Short Interfering Ribonucleic Acids (siRNAs)

siRNAs can be designed to target several debilitating diseases. Inhibiting a target protein using siRNA's can effectively down regulate either the function of an individual gene or group of genes without eliciting a toxic or an immune response. Post-transcriptional gene silencing occurs through RNA interference, where the double stranded RNAs (dsRNAs) are cleaved into 21-23 nucleotide fragments (i.e., short interfering RNA: siRNA). Cleavage occurs by a cellular endonuclease of the ribonuclease-Ill type called DICER. The short duplexed siRNA's are unwound by a helicase with the antisense strand becoming incorporated into the multi-component RNA-induced silencing complex (RISC). This moiety mediates sequence-specific gene silencing by cleaving the target mRNA.

A siRNA phosphodiester backbone is anionically charged and naked siRNA does not pass through the cell membrane. The electrostatic repulsion between naked siRNA and the anionic cell membrane surface prevents naked siRNA endocytosis. Therefore, a delivery system is required for efficient transport and release. The most commonly used gene delivery systems can be divided into biological (viral) and nonbiological (non-viral) systems. Each group has its own advantages and limitations. Biological carriers and viruses possess high efficiency in siRNA transfer but are difficult to produce and may be toxic. These limitations favor nonbiological systems for siRNA delivery.

Non-viral delivery systems including peptides, lipids (liposomes), dendrimers and polymers with cationic charges that interact with the negatively charged siRNA through electrostatic interactions. A recent review focused on use of precise polymer conjugates as nucleic acid delivery and concluded that the materials for delivery of siRNA had to be precise polymers, with defined site-specific conjugation strategies that provided multifunctional conjugates for nucleic acid transport. Dendrimers, defined peptide carriers, sequence-defined polyamidoamines assembled by solid-phase supported synthesis, and precise lipopeptides or lipopolymers have been characterized for pDNA and siRNA delivery. Conjugation techniques such as click chemistries and peptide ligation are available for conjugating polymers with functional transport elements such as targeting or shielding domains and for direct covalent modification of therapeutic nucleic acids in a site-specific mode. However, the efficacy of RNAi in vivo depends upon efficient delivery of the intermediates of RNAi, such as short interfering RNA (siRNA).

Short inhibitory RNA's targeting the gram-negative LpxC gene.

Inhibiting target protein synthesis using siRNA's can effectively down regulate either the function of an individual gene or group of genes without eliciting a toxic or an immune response. Thus by inhibiting expression of the LpxC gene using siRNA, bacterial cell wall synthesis is prevented and infectious sequalae will be prevented or aborted. The mechanism involves unwinding the short duplexed siRNA's by a helicase with the antisense strand becoming incorporated into the multi-component RNA-induced silencing complex (RISC). This moiety mediates sequence-specific gene silencing by cleaving the target mRNA. Several sequences in the LpxC gene from both *E. coli*, *P. aeruginosa* and several other gram-negative enteric bacteria have been identified. siRNA's will be constructed from these sequences and employ the siRNA's to treat infections induced by these and other strains of bacteria.

Exemplary siRNA's are described below.

```
siRNA #3
mRNA                AGGGTGACGTCAAAGTGGATACG sense siRNA         5': GGUGACGUCAAAGUGGAUA 3'

Anti sense siRNA    3': TdT CCACUGCAGUUUCACCUAU
```

Blast analysis indicates alignment complete alignment (100%) for the coding sequence of the LpxC gene (UDP-3-O-acyl-N-acetylglucosamine deacetylase) against multiple strains of *Pseudomonas aeruginosa* and should prove effective against all *P. aeruginosa*.

*Pseudomonas aeruginosa* has become an important cause of infection, especially in patients with compromised host defense mechanisms. It is the most common pathogen isolated from patients who have been hospitalized longer than 1 week. It is a frequent cause of nosocomial infections such as pneumonia, urinary tract infections (UTIs), and bacteremia. Pseudomonal infections are complicated and can be life threatening,

```
siRNA #4
mRNA:               GACTTGAATCCACCGGTAGATTT

Sense siRNA         5': CUUGAAUCCACCGGUAGAUdTdT

Anti Sense siRNA    3': TdTdGAACUUAGGUGGCCAUCUA
```

Blast analysis indicates efficacy against all strains of *E. coli*. Analyses shows further complete alignment against at least 21 strains of *Salmonella* and several strains of *Shigella*, *Klebsiella* and *Enterobacter*. The most frequent bacterial cause of urinary tract infection (UTI) in adult women is *Escherichia coli*, which is part of the normal gut flora. This organism accounts for approximately 85% of community-acquired UTIs and 50% of hospital-acquired UTIs. Other common organisms include *Klebsiella pneumoniae*, *K. pneumoniae* has been a recognized pulmonary pathogen since its discovery >100 years ago.

*Klebsiella pneumoniae* is among the most common gram negative bacteria encountered by physicians worldwide. It is a common hospital-acquired pathogen, causing urinary tract infections, nosocomial pneumonia, and intraabdominal infections. *K. pneumoniae* is also a potential community-acquired pathogen.

*Enterobacter* species, particularly *Enterobacter cloacae* and *Enterobacter aerogenes*, are important nosocomial pathogens responsible for various infections, including bacteremia, lower respiratory tract infections, skin and soft-tissue infections, urinary tract infections (UTIs), endocarditis, intra-abdominal infections, septic arthritis, osteomyelitis, and ophthalmic infections. *Enterobacter* species can also cause various community-acquired infections, including UTIs, skin and soft-tissue infections, and wound infections, among others.

*Shigella* bacteria produce toxins that can attack the lining of the large intestine, causing swelling, ulcers on the intestinal wall, and bloody diarrhea.

*Salmonella enterica* serovar *Typhimurium*, is the causative agent of typhoid fever. *Salmonella enterica* serovar *Typhimurium* is the most common cause of food poisoning by *Salmonella* species. *Salmonella* infections are often fatal if they are not treated with antibiotics.

```
siRNA #5
mRNA:              GAGCATGATGTACGGATTTCAAC

Sense siRNA        5': GCAUGAUGUACGGAUUUCAdTdT

Anti Sense siRNA   3': TdTdCGUACUACAUGCCUAAAGU
```

Blast analysis indicates efficacy against all strains of *E. coli*. Further analyses show complete alignment against *Salmonella* and several strains of *Shigella*.

Polymyxins are cyclic polypeptide antibiotics. In addition to their bacteriocidal properties they bind to the lipid A portion of endotoxins and block their biologic properties. Low doses of polymyxin B have been used therapeutically in burn patients to neutralize circulating endotoxin consequent to burn injury. Low concentrations of polymyxin bound to a dextran-poloxamer nanogel will not present a toxic problem, in contrast to the therapeutic doses of Colistin, structurally related to polymyxin, currently in use. The lipopolysaccharides (LPS) of gram negative bacteria function to provide membrane stabilization, integrity and confer resistance to host defenses. LPS is critical to the proliferation of gram-negative bacteria and disruption, mutation or removal of LPS results in bacterial death. All gram negative bacteria exhibit LPS in their outer membrane. LPS is composed of complex carbohydrates and lipid A. The carbohydrates vary in structure and confer the antigenic properties which distinguish different bacterial strains. The Lipid A is highly conserved across strains and is responsible for many of the pathogenic, immunologic and pyrogenic effects of gram negative bacteria The ubiquitous nature of LPS makes it an attractive target for treatment of nearly all Gram-negative bacterial strains. Lipid A is a critical structural component of LPS. It functions to anchor LPS to the cell membrane and it is structurally bound to the core polysaccharide.

The synthesis of the KDO lipid A complex is under control of a series of several constitutively expressed enzymes. These are LpxA, LpxC, LpxD, Lp H, LpxB, LpxK, LpxL and LpxM. Not all bacteria possess all of these enzymes but the first four are commonly expressed in gram negative bacteria. Lpx C is a zinc-dependent deacylase (UDP-(3-0-(R-3-hydroxymyristoyl))-N-acetylglucosamine deacylase). It is the first committed step in Lipid A biosynthesis and has been shown to be essential for growth of *E. coli*. Indeed several labs have focused on the antibacterial properties of pharmacologic agents which inhibit LpxC enzymatic activity, (antimicrob. Agents Chemother. 50: 2178, 2006, Curr. Pharm Biotechnol. 9; 9, 2008) Antimicrobial resistance mechanisms have been reported for all known antibacterial drugs that are currently available. Thus the inventors have focused their attention of strategies on the development of new and more effective agents that bypass the threat of antibiotic resistance by inhibiting the expression of the LpxC gene.

Polymyxin B conjugated to an embodiment of the poloxamer-polysaccharide hydrogel produces a safe, effective, in vivo nanotherapeutic platform for targeting and killing gram negative bacteria through controlled delivery of nondrug antibacterial compounds, e.g., siRNA, PVP-I, Silver.

TABLE 1

| Site | Prodrug | Mode of Action |
| --- | --- | --- |
| Cell membrane | Polymyxins | Phospholipids |

Additional Gram Negative Targeting Prodrug Conjugations for Dextran Comonomer of Polysaccharide-Poloxamer to Deliver Antibiotics Penicillin, Cephalosporin, and Glycopeptide are r-lactam antibiotics that inhibit bacterial cell wall biosynthesis and afford an opportunity as potential conjugates of the polysaccharide-poloxamer drug delivery system to target the multiple drug resistant bacteria. The other antibiotics act in the cell and to be effective these antibiotics must penetrate the cell wall. Aminoglycosides, for example, have to be actively transported across the bacterial cell membrane. Glycoproteins, for example, vancomycin and teicoplanin, are unable to penetrate the outer membrane of gram-negative organisms and thus have restricted activity against these organisms. Conjugation to a polysaccharide-poloxamer nanogel may allow these antibiotics to pass through the cell wall, be released, and effectively kill the bacteria.

TABLE 2

| Site | ProDrug | Mode of Action |
| --- | --- | --- |
| Cell wall | Penicillins | Transpeptidase |
|  | Cephalosporins | Transpeptidase |
|  | Glycopeptides | Acyl-D-alanyl-D-alanine |
|  | Carbapenem | |

Example 9: Amine Conjugation on Polysaccharide-Poloxamer Hydrogel for Cationic Charged Nanogel Delivery Amines may also be conjugated to the polysaccharide-poloxamer nanoparticles or hydrogel. Cationically charged compounds may then be chemically attached to the nanoparticles or hydrogel. Nanoparticles with a primary amine at the surface promote higher rates of phagocytic uptake. To produce a charged Polysaccharide-poloxamer nanoparticle, an amine can be conjugated to dextran prior to polymerization (as discussed in Example 9) or the surface of the nanoparticle may be functionalized after polymerization.

To incorporate amine group into dextran-acrylate (Example 2), dextran-acrylate may be further reacted with 3-CHLOROPROPYLAMINE HYDROCHLORIDE in the presence of triethylamine. An example of dextran-acrylate-propylamine synthesis is given here:

Pre-dried dextran-acrylate (2.0 g) will be dissolved in anhydrous DMSO under nitrogen gas at room temperature. Triethylamine (11.2 ml) was then injected into the above solution. Meanwhile, 3-chloropropylamine hydrochloride (4.8 g) will be dissolved in DMSO and then added to the above solution drop wise, and stirred for 5 hours at 50° C. Dextran-acrylate-propylamine will be obtained by precipitating the filtered solution into excess cold isopropyl alcohol. The product was further purified three times by dissolution/precipitation with DMSO/cold isopropyl alcohol. The final product was dried overnight at room temperature under vacuum before further use.

"Charged"-siRNAs or other charged medicaments or targeting agents may then be chemically attached to or encapsulated in the amine functionalized polysaccharide-poloxamer nanoparticle produced from the amine functionalized dextran-acrylate and delivered as targeted cargo to bacteria.

Example 9: Antibody Conjugated Polysaccharide-Poloxamer Nanoparticles for Treatment for Treatment of Triple Negative Breast Cancer Triple negative breast cancer (TNBC) is an aggressive breast cancer phenotype characterized by lack of expression of estrogen receptor (ER) and progesterone receptor (PR), as well as the absence of overexpressed human epidermal growth factor receptor-2 (HER-2) (1. de Ruijter et al). As noted below, this threatening disease is far reaching in its effects. About 15% of breast cancer patients are diagnosed with triple negative breast cancer. An estimated 1 million cases of breast cancer are diagnosed annually worldwide. Of these, approximately 170,000 are of the triple-negative (ER-/PR-/HER2-) phenotype. Of these TNBC cases, about 75% are "basal-like."

TNBC is generally accepted as a clinical surrogate for basal-like breast cancer. All basal-like breast cancers are not triple negative however. This phenotype is associated with an early age of cancer onset, high chance of presentation with metastases and high proliferative index (Nofech-Mozes et al). The prognosis of patients with this type of tumor is very poor because of non-responsiveness to hormonal therapy or poor response to the therapy of choice in breast cancer—Tamoxifen. Hence, there is an urgent and unmet need for efficacious therapeutics to treat TNBC. Anti-EGFR therapy has been increasingly recognized as an important treatment for TNBC patients and is being evaluated in advanced clinical trials for patients with metastatic TNBC. High expression of epidermal growth factor receptor (EGFR) induces erroneous development and unrestricted proliferation in a number of human malignancies, including breast cancer and also prostate cancer. This receptor has long been considered as a potential target for the treatment of a number of cancer types. EGFR mRNA is detected more frequently and at higher levels in basal-like breast cancers. Antibody dependent cellular cytotoxicity is recognized as prominent cytotoxic mechanism for therapeutic monoclonal antibody. There are a number of monoclonal antibodies (mAbs) currently available on the market for cancer treatment and a plethora being evaluated in clinical trials exhibiting mixed therapeutic outcomes. For an optimum therapeutic response, monoclonal antibodies (mAbs) should exhibit a sufficiently long half-life to interact with the target tissue effectively, have the capability to get internalized in the tumor interior, have no inducement of an immune response, and deliver sufficient potency (16. Manuel et al). Unfortunately, most of the marketed mAbs do not fulfill all of these requirements, thus providing a suboptimal therapeutic response.

Nanotechnology is an area of manipulation/construction of structures in a nanometer size range. The chemical/physical properties of the construct can radically change at this level, which can be exploited to deliver the antibody to uncharted destinations efficiently and also carry more antibodies precisely to the site of action which will elicit greater effect. An antibody capable of identifying tumor antigens can be anchored on the surface of the nanocarriers to increase the targeting efficiency, thereby increasing drug accumulation in the tumor tissue. These antibody conjugated nanocarriers can provide long circulation and significantly higher tumor accumulation properties (due to enhanced permeability retention effect) which yield significant improvements in therapeutic efficacy.

Some of the other examples of marketed antibody conjugates are with cytotoxic drugs (Mylortag®) or radioisotopes (ProstaScint®). However, to date, there are no commercial antibodies conjugated to nanoparticles available in the cancer treatment regimen. The available data suggests a significant edge of antibody conjugated nanoparticles in cancer therapy in terms of efficacy and a reduction in toxicity. The treatment of TNBC presents a momentous challenge to the oncologist often faced with limited therapeutic options coupled with aggressive and unresponsive tumors. Thus, development of an efficient therapeutic system for effective treatment modality of TNBC is an urgent need. This could be addressed by conjugating clinically relevant antibody to nanoparticles.

A therapeutic modality for the treatment of TNBC in the form of EGFR antibody conjugated to polysaccharide-poly (epoxide) nanoparticles will be developed to yield significant therapeutic benefit over current therapies.

A revolutionary new biocompatible hydrogel drug delivery platform based on a polymeric network of cross-linked polysaccharide monomers and epoxide monomers will be used to form nanoparticles. In a particular embodiment, a hydrogel synthesized from crosslinking a modified dextran (a natural polymer) and another FDA approved polymer (Pluronic® F-127) also modified to facilitate (esterification) UV crosslinking will create the new copolymer hydrogel. Pluronic® F-127 is biodegradable and also provides thermally responsive properties when incorporated into the nanoparticle. The elevated and narrow range of human body temperature offers an ideal trigger for thermal responsive hydrogels that employ the block copolymer Pluronic® F-127 obtained from BASF and offers "tunable optimization" per application for "tailored" controlled therapy. This hydrogel is amenable for conversion to nanoparticles either by lop down or bottom up approaches with narrow particle size distribution.

An alternative to the UV crosslinked hydrogel procedure is production of the hydrogels by inverse miniemulsion polymerization and crosslinked in-situ by free radical mechanisms. The advantage of this approach is a lesser energy demand of the process and the elimination of the need for high energy equipment. The polysaccharide-poloxamer platform (in specific embodiments, dextran-pluronic F-127 nanoparticle) also offers "tunable" optimization of the nanogels for different applications for "tailored" controlled therapy. Embodiments of the nanoparticle and/or hydrogel is amenable for formation to nanoparticles either by a "top down" or a "bottom up" approach to produce nanoparticles of narrow particle size distribution. A bottom-up approach constructs nanoparticles from basic building blocks like atoms or molecules as in a miniemulsion polymerization process. A top-down approach produces nanoparticles from larger materials from physical processes such as, for example, grinding or milling or through chemical-based processes (bond breaking).

EGFR antibody conjugated nanoparticles derived from polysaccharides and poloxamers would yield better therapeutic response in TNBC due to the following:

These mAb conjugated nanoparticles would exhibit higher accumulation at the tumor site due to an enhanced permeability effect;
The hydrophilic surface of the nanoparticles would render them long circulating (Karmali et al); and Biocompatible cargo is not expected to yield any toxicity or immune reactions (van Manen et al).

These properties of embodiments of the polysaccharide-poly(epoxide) nanoparticles may result in better treatment of TNBC. Commercially available or clinically evaluated EGFR mAb would be preferred, as it would propel the development cycle significantly and shorten the time for market entry. The EGFR mAb may be selected from, but not limited to, Cetuximab (Harding et al, Vincenzi et al), Panitumumab (Ferraro et al, Carteni et al) or Zalutumumab (Rivera et al). The nanotechnology will yield viable options to otherwise non responsive and aggressive TNBC. Hence, embodiments of the polysaccharide-poly(epoxide) will yield a therapeutically efficient, commercially viable niche formulation to treat TNBC with a scope of extending the indications to other cancer types exhibiting EGFR overexpression such as prostate cancer.

Example 9A

Formulation of Polysaccharide-Poloxamer Nanoparticles

In this embodiment, a "bottom up" technique for formation of nanoparticles using inverse emulsion polymerization will be used to produce the polysaccharide-poloxamer nanoparticles. This technique has been developed and optimized. The inverse emulsion polymerization technique selected for the production of nanoparticles is simple, versatile and easy to scale-up. The size of the macromonomer inverse emulsion droplets can be manipulated by varying emulsifier concentration. In this embodiment, polysaccharide-poloxamer nanogels of desired size may be produced with the controlled droplets of water soluble dextran-acrylates UV cross-linked to Pluronic® F-127 diacrylates in solution. Photopolymerization proceeds very fast but irradiation may be allowed to proceed for an extended time, such as for 1 hour to ensure substantially complete polymerization.

Other polysaccharides can be cross-linked to Pluronic® F-127 or other poloxamers (or more generally poly(epoxides), in inverse emulsion photopolymerization, provided they are soluble in water and that the monomers contain, or are functionalized with, polymerizable groups.

Dextran-pluronic F-127 nanoparticles, other polysaccharide-poloxamer, or polysaccharide-poly(epoxide) based hydrogels can be obtained via inverse emulsion photopolymerization. Nanoparticle size can be controlled through choice of emulisifer(s), monomer and emulsifier concentration, and polymerization process conditions.

Example 9B

Conjugation of EGFR Antibody to Dextran-Pluronic F-127 Nanoparticles, Other Polysaccharide-Poloxamer, or Polysaccharide-Poly(Epoxide) Nanoparticles In this embodiment, EGFR antibody will be conjugated to the surface of dextran-pluronic F-127 nanoparticles after formation of the nanoparticles. Alternatively, the EGFR antibody may be conjugated to the monomers with subsequent formation of nanoparticles. A mAb within the nanoparticle matrix would elicit therapeutic response after degradation of the nanoparticle. The surface pendent mAb recognizes the target receptor and attaches to them to elicit bioactivity of the cell.

The Fc-directed conjugation of the antibody molecules would be made through reductive amination coupling between the free amino groups in the Fc-region of the antibody and reactive aldehyde groups. To create reactive aldehyde groups on the nanoparticles surface, oxidation of dextran may be carried out under mild conditions using sodium iodate and a fixed concentration of dextran-pluronic F-127 nanoparticles. This reaction may be performed in the dark and under an inert atmosphere. The oxidation reaction will be quenched by the addition of ethylene glycol. The nanoparticles will be purified by dialysis. To this, different concentrations of EGFR antibody will be added and incubated. This conjugated structure will be stabilized by reduction using sodium borohydride. Finally, the nanoparticles will be purified and concentrated using spin filter (Rezaeipoor et al). Optionally, fluorescent tagged mAB will also be used as marker for cellular uptake and trafficking study.

Example 9C

Determination of Antibody Concentration on the Nanoparticle

The final antibody/nanoparticle ratio will be determined using a bicinchoninic acid (BCA) assay (Protein Quantitation Assay, Pierce).

Example 9D

Physiochemical Characterization of mAB Conjugated Dextran-Pluronic F-127 Nanoparticles The size and zeta potential of dextran-pluronic F-127 nanoparticles will be evaluated by dynamic light scattering technique. This technique will also be used to determine any changes in the nanoparticles' characteristics due to mAb conjugation. The shape of nanoparticles will be accessed by transmission electron microscopy after negative staining with uranyl acetate or phosphotungstic acid or osmium tetroxide. Surface characteristics of mAb conjugated dextran-pluronic F-127 nanoparticles will be done to evaluate the effect of the conjugation process.

Example 9E

In Vitro Cell Culture Studies

A number of different cell lines will be used to evaluate the developed mAb conjugated dextran-pluronic F-127 nanoparticles. The cell lines evaluated will include human breast cancer cell lines MDA-MB-468 (TNBC, EGFR-positive), SKBR-3 (EGFR-positive), BT-474 (EGFR-positive), and MCF-7 (EGFR-negative). The dextran-pluronic F-127 nanoparticles conjugated with different mAb concentrations, naked mAb, and unconjugated dextran-pluronic F-127 nanoparticles will be evaluated in different cell culture studies such as proliferation assay, cell cycle assay, and western blot analysis and the cell uptake will be evaluated by (fluorescent conjugated mAb) flowcytometry, confocal microscopy, etc.

These studies will be designed to check retention of bioactivity of mAb after the conjugation process, and optimization of mAb concentration on the dextran-pluronic F-127 nanoparticles to yield optimal bioactivity. In vitro and in vivo evaluation of three prototype EGFR monoclonal antibody conjugated dextran-pluronic F-127 nanoparticles will be performed. The primary objective of these studies is to determine anti-tumor activity of these novel reagents with a model of breast cancer that is EGFR positive and is ER-PR- and HER2-. In this model we will determine whether the antibody targeting EGFR conjugated to dextran-pluronic F-127 superior efficacy compared to the unconjugated antibody because it would have better bioavailability and deliver better properties than conventional formulations, which would in turn translate to better tumor growth inhibition.

Prior to in vivo efficacy testing of these novel nanoparticles it will be important to determine their safety upon intravenous delivery to immunocompromised athymic nude mice. Also, prior to evaluating in vivo tolerability of the antibody conjugated nanoparticles, we will test their toxicity in vitro. First, we will perform the MTT assay with the MDA-MB-468 breast cancer cells that will be utilized in the in vivo efficacy study. Hemolysis and micronucleus test of genotoxicity will be performed.

Example 9F

In Vitro Toxicology Studies

Evaluation of toxicity of dextran-pluronic F-127 nanoparticles is an important step in development of any nanotechnology based therapeutic agent. (Arora et al, Kroll et al, 2009, Kroll et al, 2012). In vitro model systems provide a rapid and effective means to assess nanoparticles for specific toxicological endpoints. These studies allow for elucidation of the mechanism of interaction of nanoparticles with cells. Hence in vitro studies can be effectively used to establish specific toxicological profiles of developed nanoparticles and would help to design the protocol of in vivo studies.

Using the established protocol (Zhang et al), the MTT assay will determine the effect of two-three prototypes antibody conjugated nanoparticles on MDA-MB-468 cell viability and metabolic activity measured by the reduction of the tetrazolium salt MTT to insoluble MTT-formazan. The unconjugated dextran-poloxamer nanoparticles will also be tested as control. Moreover the hemolysis (Zhang et al, Yu et al) and micronucleus genotoxic test (Gonzalez et al) will measure different cytotoxicity endpoints of the antibody conjugated dextran-poloxamer nanoparticles.

The results from these studies will allow us to select the optimal concentration of the antibody formulation that will be tested in the in vivo efficacy and compared with the naked antibody, control unconjugated nanoparticles and saline.

Example 9G

In Vivo Tolerability Study in Female Athymic Nude Mice

In this study mice will receive treatment intravenously twice a week, and will be carefully observed every day for at least two weeks for any sign of distress, abnormal behavior, body weight loss, morbidity, and mortality. Gross examination of organs will be done. The results from this study will be useful to assess safety of antibody conjugated nanoparticles in mice prior to testing their efficacy.

Example 9H

In Vivo Efficacy Study in Female Athymic Nude Mice

The MDA-MB-468 tumor cells implanted in mice for this study will be first transfected with the luciferase lentiviral particles and implanted into the mammary fat pad of five mice to ensure the tumors grown in vivo retain bioluminescence. Then the luciferase-labeled tumor cells will be harvested from in vitro cultures and implanted with 50% matrigel in the mammary fat pads of nude mice (left side, 5×106 per mouse). When the tumors reached an average size of at least 130 mm3 the mice will be randomized and distributed into 5 groups of 10 mice/each group with similar tumor size and bioluminescent signal measured by the Lumina Instrumentation after intraperitoneal injection of D-luciferin (15 mg/ml, 200 µl). The five treatment groups are two prototype mAB conjugated polysaccharide-poly (epoxide), polysaccharide-poloxamer, or dextran-pluronic F-127 nanoparticles formulations, the unconjugated monoclonal antibody, the unconjugated nanoparticles, and saline. Treatment will be delivered intravenously twice a week for 4 weeks. The tumors will be calipered one a week or more often, and imaged with the Lumina Instrument once a week; at the end of the study, the mice will be euthanized three days after last treatment and the tumors will be harvested and fixed in 10% formalin for histology and analysis of tissue morphology. (Inoue et al, 33. Mitsunaga et al).

Example 9I

Animal Models

The tumor targeting efficacy will be evaluated by non-invasive imaging techniques. The toxicology profile of the formulation will be generated in a suitable animal model. The process for preparing the mAb conjugated polysaccharide-poloxamer nanoparticles will be optimized in view of scale up activities. Studies to convert the optimized nanoparticulate formulation into patient administrable dosage form will be initiated. Also, container closure selection study will be initiated. Analytical methods used in formulation evaluation will be validated.

Example 10: Mannosylation of Dextran-Pluronic F-127 Hydrogel

Tuberculosis (TB) is the leading cause of death in the world from a bacterial infectious disease. The disease affects 1.8 billion people yearly, equal to one-third of the entire world population.

The treatment of tuberculosis requires long-term antibiotic therapy. Because administration of a single drug often leads to the development of a bacterial population resistant to that drug, effective regimens for the treatment of TB must contain multiple drugs to which the organisms are susceptible. Active tuberculosis, particularly if it's a drug-resistant strain, will require several drugs at once. The most common medications used to treat tuberculosis include, but are not limited to, Isoniazid, Rifampin (Rifadin, Rimactane), Ethambutol (Myambutol), and Pyrazinamide.

*Mycobacterium tuberculosis* (MTB) is the etiologic agent of tuberculosis in humans. Humans are the only reservoir for the bacterium. Targeted antibiotic therapy improves the efficacy of treatment by concentrating the drugs close to *mycobacterium*. Once attached to a macrophage, the causative agent of tuberculosis, MTB avoids cellular defenses and uses the cell to replicate. The high concentration of lipids in the cell wall of *Mycobacterium tuberculosis* has been associated with impermeability to stains and dyes, resistance to many antibiotics, resistance to lethal oxidations and survival inside of macrophages. Polysaccharide-poloxamer targeting of MTB is accomplished by using mannose as a homing device.

Mannosylation of the dextran monomer enables the multidrug releasing delivery system, Polysaccharide-poloxamer, to target the macrophage. Ref. Clemens, D. L, and M. A. Horwitz. 1996. The *Mycobacterium tuberculosis* phagosome interacts with early endosomes and is accessible to exogenously administered transferrin. J. Exp. Med. 184.1349-1355.

The development of a polysaccharide-poloxamer delivery vehicle is based on dextran linked to mannose, to target the macrophage, for multidrug therapeutic release into the phagosomal vacuole. Water-soluble polysaccharide-poloxamer hydrogel can accommodate mannose homing residues (endocytosis by the target cell via a specific receptor) thus increasing the affinity for the target. Ref. Kéry, V., J. J. F. Krepinsky, C. D. Warren, P. Capek, and P. D. Stahl. 1992. Targeting is accomplished through ligand recognition by purified human mannose receptors. Arch. Biochem. Biophys. 298:49-55.

To synthesize MTB targeted nanogels and/or nanoparticles, the monomers such as, but not limited to, the dextran monomer of the polysaccharide-poloxamer drug delivery carrier may conjugated to mannose which acts as a targeting agent to direct multiple antibacterial releasing Polysaccharide-poloxamer into macrophages.

Example 10A

Dextran $NO_2$—$NH_2$ Conjugation

Dextran (Pharmacia, Uppsala, Sweden) was can be purified to get fractions with weight-average molar masses of 64,000, 90,000, or 95,000 g/mol and with a weight-average molar mass/number-average molar mass ratio of 1.2.

Poloxamer: Pluronic F-68 BASF.

For this purpose, norfloxacin has been linked to mannosylated dextran using a peptide spacer arm. This conjugate shows more efficacy against *mycobacterium* than plain norfloxacin.

Scheme 7: Mannose Conjugated Dextran Mannosylated Synthesis.

Example 11: Methods of Producing a Polysaccharide-Poloxamer Nanoparticle

The polysaccharide and poloxamer may be cross-linked with any polymerization process or appropriate cross-linking reaction including radical polymerizations, emulsion polymerizations, inverse miniemulsion polymerization, controlled polymerization, UV initiated cross-linking, e-beam curing, ionic gelation polymerization or other polymerization process. The process, component concentrations and the process parameters may have a significant effect on the properties of the hydrogel or nanoparticles such as, but not limited to, rates of diffusion of the pharmaceuticals out of the hydrogel membrane.

The ratio of polysaccharide to poly(epoxide), the molecular weight of the polysaccharide and/or the poly(epoxide), the chemical composition of the polysaccharide and/or the poly(epoxide), the relative lengths of the ABA block of the poloxamer, the degree of self-organization prior to cross-linking, the cross-linking functionality, as well as other factors may affect the physical and chemical properties of the hydrogel. For example, the mechanical strength of the hydrogel or polymeric network can be adjusted by more or less polysaccharide (in some embodiments, dextran) which will produce a different hydrogel or polymeric network with different mechanical strength and a different time controlled delivery of a drug for drug delivery applications. The chemical composition and size are important factors, which are indicative of the capability of the particles to penetrate into biological cells.

An inverse miniemulsion polymerization process for the production of nanoparticles is preferred because it is simple, versatile and easy to scale-up. A number of different monomers may be included in the cross-linked, hydrogel network of the nanoparticles, providing a flexible way of regulating material properties and introducing functionality, incorporating electrostatically charged and reactive functional groups by copolymerization of appropriate monomers. Inverse emulsion photopolymerization is a controllable method for preparing "more defined" nanoparticles. The aqueous macromonomer nano-droplets are "stabilized" by a cross-linking polymerization of acrylic derivatives, which preserves the structure of the nanoparticles. The nanoparticles produced present a capacity (nanodomain) of incorporating hydrophobic drugs.

In one embodiment, the aqueous phase, containing eosin Y (sensitizer), triethanolamine (initiator) and Pluronic F-127 diacrylate mixed with dextran diacrylate, is dispersed in hexane by sonication with the utilization of the powerful surfactant, Span 65, in the oil-to-water protocol. After photopolymerization, nanoparticles can be by removed from the hydrophobic emulsifier through repeated n-hexane washing.

The surfactant, Span65, is dissolved in hexane by sonication. Nonionic surfactants such as Span and/or Tween may be used in the reaction media. An aqueous solution of dextran acrylate, Pluronic F-127 diacrylate, triethanolamine, and eosin Y is added to the oil phase (oil-to-water weight ratio=65/35) and an inverse emulsion can be formed. The inverse emulsion can be illuminated with an Ar ion laser for 1 hour, at room temperature, under magnetic stirring (400 rpm). After illumination, the inverse emulsion can be poured into centrifuge tubes containing n-hexane and water. The aqueous phase is extracted with n-hexane to remove the surfactant and then dialyzed against water to remove the initiator and non-reacted macromonomers.

Again, conjugation of targeting agent(s) onto the alcohol reactive groups of the modified dextran (polysaccharide) comonomer may be a first step in the production process of targeting therapeutic nanoparticles.

Inverse emulsion polymerization process has the ability to "control nanoparticle size" distribution. The size of the macromonomer inverse emulsion droplets decreased with increasing emulsifier concentration. Polysaccharide-poloxamer nanogels of desired size are produced with the controlled droplets of water soluble dextran acrylates UV cross-linked to Pluronic® F-127 diacrylates in solution. Photopolymerization proceeds very fast but irradiation may be carried out for an extended period to ensure the desired degree of polymerization. Other polysaccharides can be cross-linked to Pluronic® F-127 in inverse emulsion photopolymerization, provided they are soluble in water and that they contain, or are functionalized with, polymerizable groups. The "stable" colloidal state of the resulting nanoparticles is maintained even after freeze drying.

Further, the nanogels and nanoparticles may be effective in cancer treatment. Progress in fundamental cancer biology has not yet been met by a comparable advancement in its clinical treatment. A fundamental reason for this discrepancy is the inability to selectively reach and eliminate tumor tissue with marginal damage to healthy organs, cancer cell targeting by polysaccharide-poloxamer drug delivery systems aims at increasing selectivity and overcoming biological barriers, while transporting higher drug amounts.

Active targeting is accomplished by attachment of specific molecules on the carrier's surface, which enhance the binding and interactions with antigens or receptors expressed on specific cell populations. Targeting ligands explored for cancer therapy include antibodies and antibody fragments which can be conjugated to Polysaccharide-poloxame for specific active targeted drug delivery.

A major class of chemotherapeutics currently used in clinical practice are the anthracycline molecules. Doxorubicin is probably the most known member of the anthracycline family. These potent anti-proliferative agents are a typical example of drugs whose efficacy is constrained by non-specific toxicities and would therefore benefit by the polysaccharide-poloxamer targeted drug delivery approach Immune response and biodegradability issues are a significant concern for drug delivery devices, as well as issues relating to drug targeting and controlled drug release. Consequently, there is an immediate need for a comprehensive answer to these problems. A dextran-poloxamer copolymer nanoparticle (nanogel) offers a universal platform that guarantees a safe, sustained, and controlled drug delivery system.

The thermal response feature of the poloxamer (Pluronic® F-127) comonomer component and the controlled release capability (various ratio compositions of dextran-poloxamer) of polysaccharide-poloxamer nanogels enable development of more effective therapeutic nanoparticles. With continuous advances in identifying new biomarkers and associated targeting ligands it will be increasingly feasible to develop targeted and controlled release nanoparticle products as promising candidates for clinical translation.

Nanoparticles comprised of polysaccharides and poloxamers offer excellent nanocarrier capabilities. Particularly, the Dextran-Pluronic nanogels exhibit ideal characteristics and features desired in a drug delivery system. They are nontoxic, nonimmunogenic, nonantigenic, and biodegradable. For targeting, especially, they present a great number of hydroxyl groups for conjugation of prodrugs, enzymes, heavy metals (e.g., Fe) and small molecules, for example.

REFERENCES

Adler M J, Dimitrov D S. Therapeutic antibodies against cancer. Hematol Oncol Clin North Am. 2012 Jun. 26(3): 447-81.

Arora S, Rajwade J M, Paknikar K M. Nanotoxicology and in vitro studies: the need of the hour. Toxicol Appl Pharmacol. 2012 Jan. 15; 258(2):151-65.

Carteni G, Fiorentino R, Vecchione L, Chiurazzi B, Battista C. Panitumumab a novel drug in cancer treatment. Ann Oncol. 2007 Jun. 18 Suppl 6:vi16-21.

Corkery 8, Crown J, Clynes M, O'Donovan N. Epidermal growth factor receptor as a potential therapeutic target in triple-negative breast cancer. Ann Oncol. 2009 May; 20(5):862-7.

de Ruijter T C, Veeck J, de Hoon J P, van Engeland M, Tjan-Heijnen V C. Characteristics of triple-negative breast cancer. J Cancer Res Clin Oncol. 2011 February; 137(2):183-92.

Del Mastro L, Lambertini M, Bighin C, Levaggi A, D'Alonzo A, Giraudi S, Pronzato P. Trastuzumab as first-line therapy in HER2-positive metastatic breast cancer patients. Expert Rev Anticancer Ther. 2012 Nov. 12(11):1391-405.

Duffy M J. Tumor markers in clinical practice: a review focusing on common solid cancers. Med Princ Pract. 2013; 22(1):4-11.

Ferraro D A, Gaborit N, Maron R, Cohen-Dvashi H, Porat Z, Pareja F, Lavi S, Lindzen M, Ben-Chetrit N, Sela M, Yarden Y. Inhibition of triple-negative breast cancer models by combinations of antibodies to EGFR. Proc Nat Acad Sci USA. 2013 Jan. 29; 110(5):1815-20.

Gonzalez L, Sanderson B J, Kirsch-Volders M. Adaptations of the in vitro MN assay for the genotoxicity assessment of nanomaterials. Mutagenesis. 2011 Jan. 26(1):185-91.

Greenberg S, Rugo H S. Challenging clinical scenarios: treatment of patients with triple-negative or basal-like metastatic breast cancer. Clin Breast Cancer. 2010 Sep. 10 Suppl 2:520-9

Harding J, Burtness B. Cetuximab: an epidermal growth factor receptor chemeric human-murine monoclonal antibody. Drugs Today (Barc). 2005 February; 41(2):107-27

Inoue S, Patil R, Portilla-Arias J, Ding H, Konda B, Espinoza A, Mongayt D, Markman J L, Elramsisy A, Phillips H W, Black K L, Holler E, Ljubimova J Y. Nanobiopolymer for direct targeting and inhibition of EGFR expression in triple negative breast cancer. PLoS One. 2012; 7(2):e31070

Karmali P P, Chao Y, Park J H, Sailor M J, Ruoslahti E, Esener S C, Simberg D. Different effect of hydrogelation on antifouling and circulation properties of dextran-iron oxide nanoparticles. Mol Pharm. 2012 Mar. 5; 9(3):539-45.

Kim E M, Jeong H J, Jeong M H, Lee C M, Cheong S J, Kim D W, Lim S T, Sohn M H, dextran-conjugated vascular endothelial growth factor receptor antibody for in vivo melanoma xenografted mouse imaging. Cancer Biother Radiopharm. 2012 Mar. 27(2):141.8.

Kroll A, Pillukat M H, Hahn D, Schnekenburger J. Current in vitro methods in nanoparticle risk assessment: limitations and challenges. Eur J Pharm Biopharm. 2009 June; 72(2):370-7.

Kroll A, Pillukat M H, Hahn D, Schnekenburger J. Interference of engineered nanoparticles with in vitro toxicity assays. Arch Toxicol. 2012 July; 86(7):1123-36.

Luedke E, Jaime-Ramirez A C, Bhave N, Carson W E 3rd. Monoclonal antibody therapy of pancreatic cancer with cetuximab: potential for immune modulation. J Immunother. 2012 June; 35(5):367-73.

Manuel Arruebo, Mónica Valladares, and África González-Fernández, "Antibody-Conjugated Nanoparticles for Biomedical Applications," Journal of Nanomaterials, vol. 2009, Article ID 439389, 24 pages, 2009, doi:10.1155/2009/439389

Mendelsohn, The epidermal growth factor receptor as a target for cancer therapy. Endocrine-Related Cancer 2001:8 3-9

Mitsunaga M, Nakajima T, Sano K, Kramer-Marek G, Choyke P L, Kobayashi H. Immediate in vivo target-specific cancer cell death after near infrared photoimmunotherapy. BMC Cancer. 2012 Aug. 8; 12:345

Nielsen T O, Hsu F D, Jensen K et al. Immunohistochemical and clinical characterization of the basal-like subtype of invasive breast carcinoma. Clin Cancer Res 2004; 10: 5367-5374.

Nofech-Mozes S, Trudeau M, Kahn H K, Dent R, Rawlinson E, Sun P, Narod S A, Hanna W M. Patterns of recurrence in the basal and non-basal subtypes of triple-negative breast cancers. Breast Cancer Res Treat. 2009 November; 118(1):131-7.

Overdijk M B, Verploegen S, van den Brakel J H, Lammerts van Bueren J J, Vink T, van de Winkel J G, Parren P W, Bleeker W K. Epidermal growth factor receptor (EGFR) antibody-induced antibody-dependent cellular cytotoxicity plays a prominent role in inhibiting tumorigenesis, even of tumor cells insensitive to EGFR signaling inhibition. J Immunol. 2011 Sep. 15; 187(6):3383-90.

Patil R R, Guhagarkar S A, Devarajan P V. Engineered nanocarriers of doxorubicin: a current update. Crit Rev Ther Drug Carrier Syst. 2008; 25(1):1-61.

Peraldo-Neia C, Migliardi G, Mello-Grand M, Montemurro F, Segir R, Pignochino Y, Cavalloni G, Torchio B, Mosso L, Chiorino G. Aglietta M. Epidermal Growth Factor Receptor (EGFR) mutation analysis, gene expression profiling and EGFR protein expression in primary prostate cancer. BMC Cancer. 2011 Jan. 25; 11:31.

Perou C M, Sorlie T, Eisen M B et al. Molecular portraits of human breast tumours. Nature 2000; 406: 747-752.

Pillay V, Gan H K, Scott A M. Antibodies in oncology. N Biotechnol. 2011 Sep. 28(5):518-29.

Rezaeipoor R, John R, Adie S G, Chaney E J, Marjanovic M, Oldenburg A L, Rinne S A, Boppart S A. Fc-directed antibody conjugation of magnetic nanoparticles for enhanced molecular targeting. J Innov Opt Health Sci. 2009 Oct. 1; 2(4):387-396.

Rivera F, Salcedo M, Vega N, Blanco Y, López C. Current situation of zalutumumab. Expert Opin Biol Ther. 2009 May; 9(5):667-74.

Tischkowitz M, Brunet J S, Begin L R et al. Use of immunohistochemical markers can refine prognosis in triple negative breast cancer. BMC Cancer 2007; 7: 134.

van Manen H-J, van Apeldoorn A A, Verrijk R, Blitterswijk CAv, Otto C, Intracellular degradation of microspheres based on cross-linked dextran hydrogels or amphiphilic block copolymers: A comparative Raman microscopy study. Int J Nanomedicine. 2007 Jun. 2(2): 241-252.

Vincenzi B, Zoccoli A, Pantano F, Venditti O, Galluzzo S. Cetuximab: from bench to bedside. Curr Cancer Drug Targets. 2010 Feb. 10(1):80-95.

Yeoman, Roy R, Fox, Adrian S, Sun, Guoming, Polymers And Hydrogels WO/2013/058778

Yu T, Malugin A, Ghandehari H. Impact of silica nanoparticle design on cellular toxicity and hemolytic activity. ACS Nano. 2011 Jul. 26; 5(7):5717-28.

Zhang Y, Chen W, Zhang J, Liu J, Chen G, Pope C. in vitro and in vivo toxicity of CdTe nanoparticles. J Nanosci Nanotechnol. 2007 Feb. 7(2):497-503.

The invention claimed is:

1. A nanoparticle targeting molecule, comprising:
a polymeric network comprising a plurality of first block copolymeric segments derived from epoxide monomers and a plurality of second polymeric segments derived from polysaccharides;
targeting agents chemically attached to the polymeric network, wherein the targeting agents comprise polyrnyxin B; and
a medicament covalently attached to the polymeric network, wherein the medicament is vancomycin.

2. The nanoparticle targeting molecule of claim 1, further comprising medicaments encapsulated within the hydrogel.

3. The nanoparticle targeting molecule of claim 1, wherein the epoxide monomers are poloxamers.

4. The nanoparticle targeting molecule of claim 3, wherein the polysaccharide is dextran.

5. The nanoparticle targeting molecule of claim 1, wherein the nanoparticle targeting molecule has an average diameter in the range of 1 nanometer to 1000 nanometers.

6. The nanoparticle targeting molecule of claim 1, wherein the nanoparticle targeting molecule has an average diameter in a range from 20 nanometers to 250 nanometers.

7. The nanoparticle targeting molecule of claim 1, wherein the epoxide monomers are poloxamers and the polysaccharide is dextran.

8. The nanoparticle targeting molecule of claim 1, further comprising a biomarker.

9. The nanoparticle targeting molecule of claim 8, wherein the biomarker is a fluorescent biomarker or a radiotag biomarker.

* * * * *